United States Patent [19]

Convert et al.

[11] Patent Number: 4,785,829

[45] Date of Patent: Nov. 22, 1988

[54] APPARATUS FOR HYPERTHERMIC TREATMENT

[75] Inventors: Guy Convert, Vincennes; Guy Azam, La Celle St. Cloud; Jean P. Mabire, Gif Sur Yvette; Claude Jasmin, Paris; Joel Sidi, Paris, all of France

[73] Assignee: C.G.R Mev, Buc, France

[21] Appl. No.: 937,559

[22] Filed: Dec. 3, 1986

[30] Foreign Application Priority Data

Dec. 10, 1985 [FR] France ................................ 85 18258

[51] Int. Cl.⁴ .............................................. A61B 1/00
[52] U.S. Cl. ................................... 128/804; 128/420 A
[58] Field of Search ............... 128/24.1, 303.1, 303.13, 128/399, 401, 402, 783, 799, 804, 420 A, 422

[56] References Cited

U.S. PATENT DOCUMENTS

| | | | |
|---|---|---|---|
| 3,096,768 | 7/1963 | Griffith | 128/420 A |
| 3,774,620 | 11/1973 | Hansjurgers | 128/420 A |
| 4,095,602 | 1/1978 | Leveen | 128/804 |
| 4,121,592 | 10/1978 | Whalley | 128/399 |
| 4,148,321 | 4/1979 | Wyss et al. | 128/420 A |
| 4,177,819 | 12/1979 | Kofsky et al. | 128/422 |
| 4,285,346 | 8/1981 | Armitage | 128/804 |
| 4,290,435 | 9/1981 | Weggat | 128/804 |
| 4,350,168 | 9/1982 | Chable et al. | 128/804 |
| 4,401,121 | 8/1983 | Radler | 128/420 A |
| 4,572,190 | 2/1986 | Azam et al. | 128/399 |
| 4,587,978 | 5/1986 | Swyame et al. | 128/804 |

FOREIGN PATENT DOCUMENTS

| | | | |
|---|---|---|---|
| 2801796 | 7/1979 | Fed. Rep. of Germany | 128/420 A |
| 3010716 | 9/1981 | Fed. Rep. of Germany | 128/420 A |
| 2052994 | 4/1982 | Fed. Rep. of Germany | 128/420 A |
| 818881 | 10/1937 | France | |
| 467502 | 6/1937 | United Kingdom | 128/420 A |
| 2171832 | 7/1983 | United Kingdom | 128/799 |

Primary Examiner—Max Hindenburg
Attorney, Agent, or Firm—Roland Plottel

[57] ABSTRACT

The invention pertains to an apparatus for hyperthermic treatment, especially designed for deep hyperthermia. The treatment apparatus comprises at least two generators operating at different frequencies in such a way as to prevent any phase correlation between the waves delivered by the generators.

8 Claims, 4 Drawing Sheets

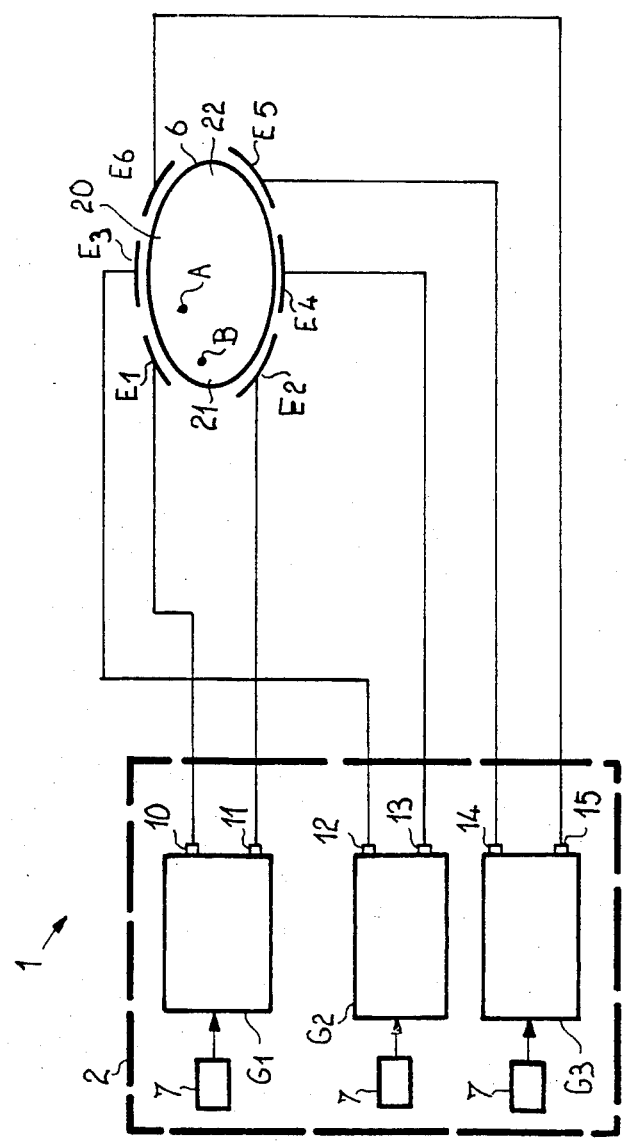

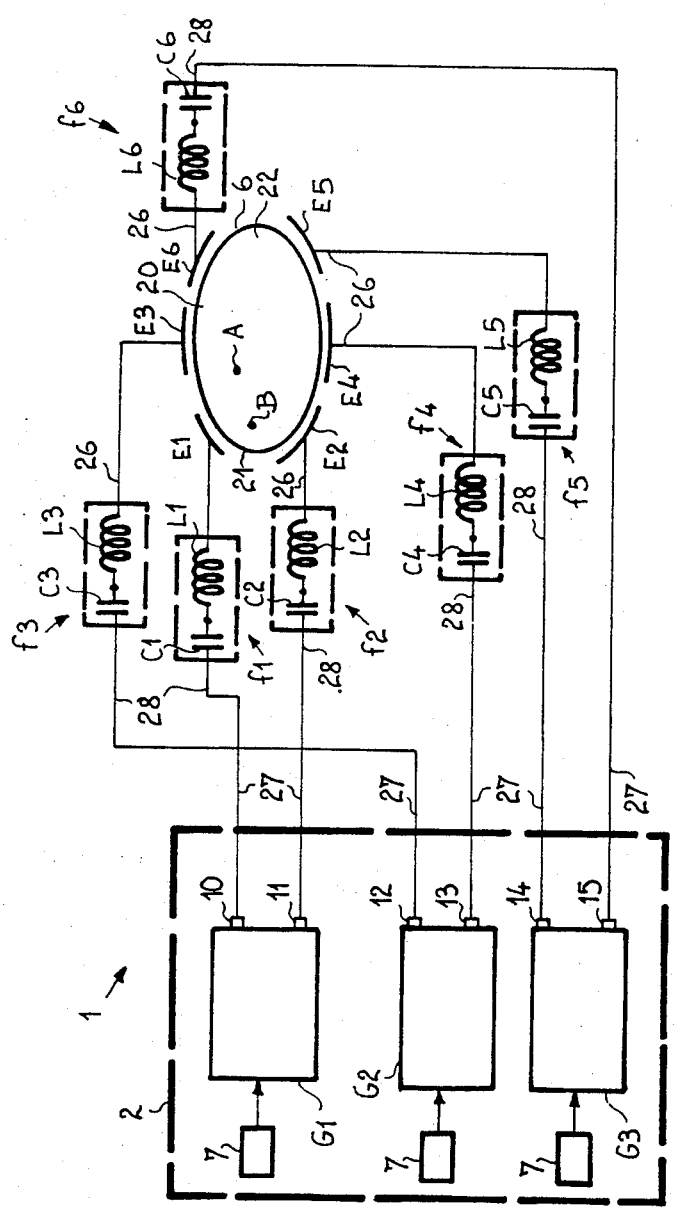

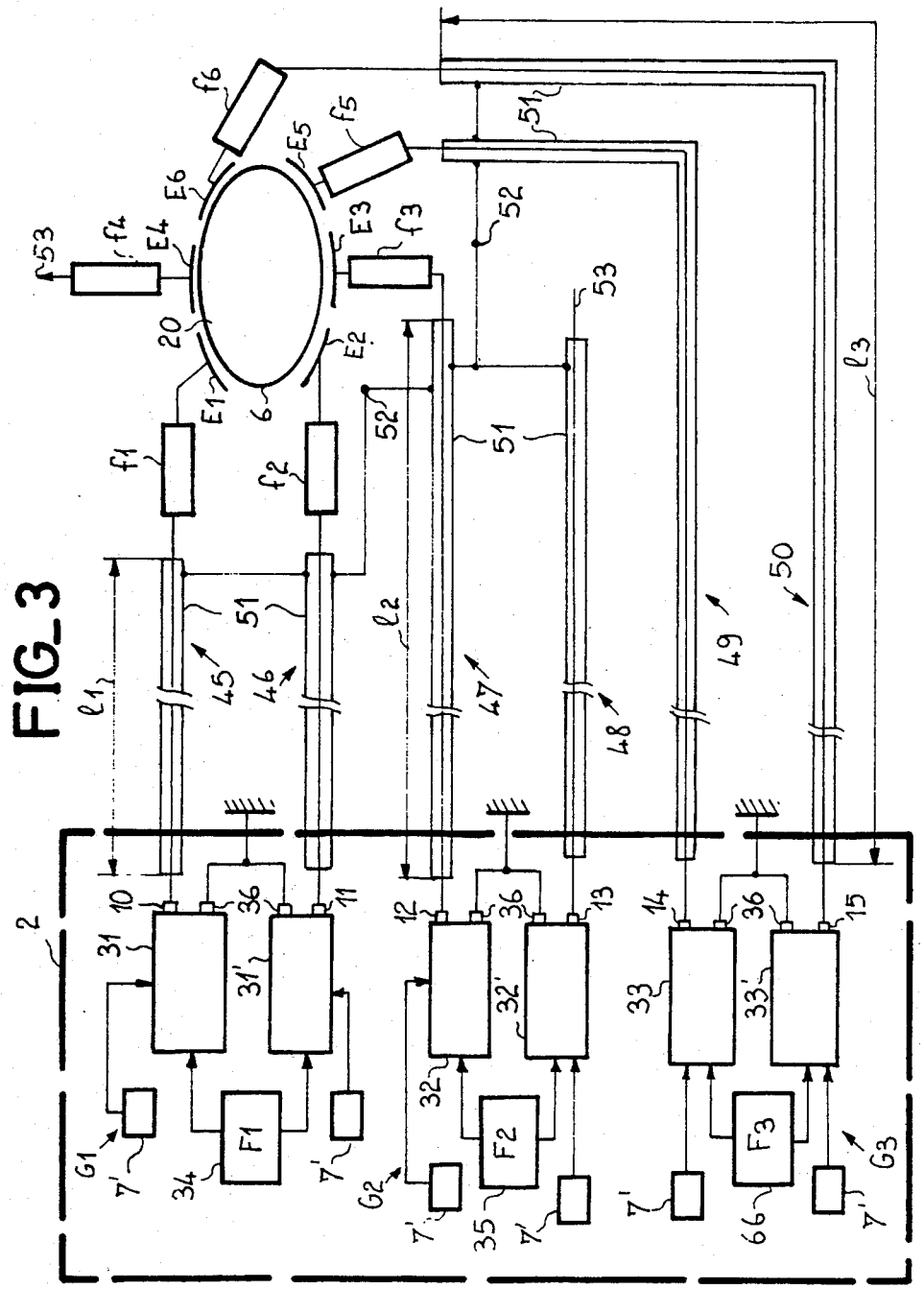

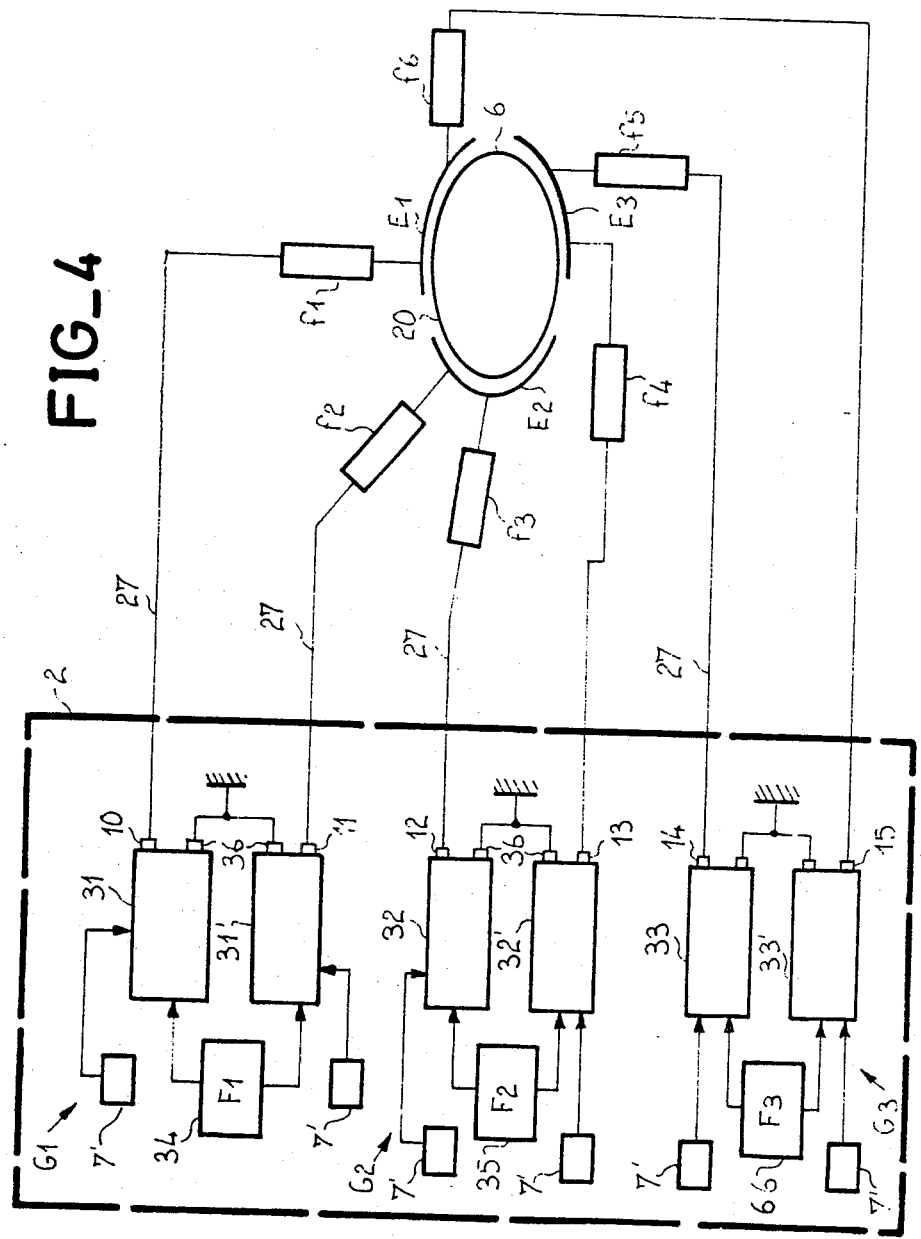

APPARATUS FOR HYPERTHERMIC TREATMENT

BACKGROUND OF THE INVENTION

The invention pertains to an apparatus for hyperthermic treatment which is especially well suited to deep hyperthermia, i.e. in cases where the part that has to be treated in a patient lies relatively deep within his body.

Hyperthermia is a method in which living biological tissues are heated, for example through the dissipation of an electro-magnetic wave applied to a part that has to be treated, using applicators laid out in the vicinity of this part. This method is used in the treatment of various diseases, especially in the treatment of cancer. In the example of the latter application, it is desirable to heat the tissues to be treated to temperatures of about 44° C. to 45° C. while at the same time avoiding, as far as possible, any marked increase in the temperature of the surrounding healthy tissues.

One of the problems that arise then is to accurately localize the heated area in relation to the area that to be treated. This condition is generally achieved satisfactorily in the treatment of superficial or shallow tumours since, in this case, the applicators placed on the patient's body are in the immediate vicinity of the area to be treated.

By contrast, in the treatment of deep-seated tumours (for example, intestinal, prostate or other such tumours), the problem of accurately localizing the power applied becomes far more acute, especially since that part of the patient which lies between two electrodes also includes healthy regions, and the problem is additionally complicated by the fact that a patient usually finds it very difficult to tolerate temperatures of more than 44° C. in the cutaneous tissues.

The technique most widely used in hyperthermia is to do the heating by means of an electro-magnetic field at frequencies which are low enough not to be limited by skin effect which prevents penetration by these electro-magnetic fields when the frequencies are greater than, for example, 50 or 60 MHZ. The applicators comprise electrodes or conductor horns or wave guides, by means of which the electro-magnetic power is applied. In outline, the heated region is the region enclosed by the electrodes or, again, in the case of a conductor horn or a wave guide, the dimensions of the heated region are approximately equal to the crosswise dimensions of the applicator. It is thus possible, in theory, to modify the distribution of the power dissipated by bringing the dimensions and position of the electrodes into play. However, the use of this method comes up against practical difficulties owing to the fact that, in a given configuration of electrodes, the distribution of the dissipated power depends on the electrical properties of the tissues to be heated. It is furthermore observed that the distribution of the dissipated power can vary a great deal for apparently small variations in the nature of the tissues to be heated. Thus, in practice, to obtain heating that is as satisfactory as possible, the practitioner must, in the very course of the hyperthermic treatment, adjust the distribution of the dissipated power, notably on the basis of data communicated by temperature probes.

To this end, a method known in the prior art through the french patent application No. 83 08727, uses high-frequency generating means comprising at least three generators which function at one and the same frequency and according to adjustable relative phases, each generator being linked to an electrode. This configuration can be used to localize a more strongly heated zone in a space surrounded by the three electrodes. One of the disadvantages of this arrangement, in which generators work at one and the same frequency with well-defined mutual phase relations, lies in the fact that field interference effects can occur in the zone to be heated, in such a way that the mean power dissipated in a given volume can be greater or smaller than the sum of the mean values of power dissipated by each generator working on its own. The result of this may be major temperature differences between two points which are relatively close to each other, with prolonged and difficult adjustments having to be made to correct these differences.

SUMMARY OF THE INVENTION

The present invention pertains to a hyperthermic apparatus, especially well-adapted to deep hyperthermic treatment, which can be used with greater precision than in the prior art to suit the configuration of the heated zone to the zone to be treated, making it possible in a flexible and sure way, either to increase the power dissipated in the treated tumour with negligible incidence on healthy regions, or on the contrary, to diminish the temperature reached in the healthy regions with minimum incidence on the temperature reached by the tumour to be treated.

In the invention, an apparatus for hyperthermic treatment comprises high-frequency generating means linked to electrodes which can be attached to a patient, wherein the said high-frequency generating means comprise at least two generators operating at different frequencies.

With several generators, each operating at a frequency which is distinct from that of the other generators, the phases of the electro-magnetic waves produced by these different generators are not mutually correlated. It is then possible, firstly, to define a zone heated by the high-frequency energies produced by each of the generators without this heated zone's displaying the disturbances caused by the previously mentioned interference effects, and secondly, to increase or decrease the power dissipated in a clearly defined part of the heated region by increasing or decreasing the power of one of the generators.

BRIEF DESCRIPTION OF THE DRAWINGS

The invention will be better understood from the following description which is given as a non-exhaustive example, and from the four appended figures of which:

FIG. 1 is a schematic depiction of a hyperthermic apparatus according to the invention;

FIG. 2 depicts the apparatus of FIG. 1, improved by means of filters;

FIG. 3 depicts a preferred embodiment of the apparatus depicted in FIG. 2;

FIG. 4 illustrates a possible mode of connection of the electrodes depicted in FIGS. 1 to 3.

DETAILED DESCRIPTION OF THE INVENTION

FIG. 1 is a schematic depiction of a hyperthermic apparatus 1 according to the invention, comprising high-frequency wave generating means 2.

According to one characteristic of the invention, the generating means 2 must comprise at least two generators G1, G2 each operating at a different frequency F1, F2 from the other. In the non-exhaustive example described, and to better illustrate the possibilities of the invention, the generating means 2 further comprise a third generator G3 operating at a third frequency F3 which is different from the first and second frequencies F1, F2.

The frequencies F1, F2 and F3 should have values which are different from one another and which are sufficiently distant from one another to prevent the generators G1, G2 and G3, which deliver power to the load represented by a patient 6, from tending to drive the frequencies of one another mutually, a factor which is liable to lead to a correlation of phases among the electro-magnetic waves delivered by the generators G1, G2, G3. Hence, the frequencies F1, F2, F3 must not only be different from one another but also have no simple relationship with one another as, for example, would be the case if they each constituted a harmonic frequency of one and the same fundamental frequency.

Each generator G1, G2, G3, is of a type known in the prior art, producing an electro-magnetic wave at a power of about 500 W for example, which can be adjusted through a power-controlling means 7 which is proper to each generator G1, G2, G3.

The generators can operate at a frequency which ranges, for example, from 100 KHertz to 50 or 60 MHertz. In the non-exhaustive example described, the first generator G1 operates at a frequency F1 equal to 5.5 MHZ, the second generator G2 operates at a frequency F2 equal to 8.5 MHZ, the third generator G3 operates at a third frequency F3 equal to 13 MHZ:

An initial output and a second output 10, 11 of the first generator G1 are respectively linked to an initial electrode and a second electrode E1, E2 forming an initial pair of electrodes;

The second generator G2 comprises a third output and a fourth output 12, 13 respectively linked to a third electrode and a fourth electrode E3, E4 forming a second pair of electrodes;

A fifth output and a sixth output 14, 15 of the third generator G3 are resectively linked to a fifth electrode and a sixth electrode E5, E6 forming a third pair of electrodes.

In the non-exhaustive example of the description, the electrodes E1 to E6 of one and the same pair of electrodes are applied to the patient 6 in such a way that they substantially face one another on either side of a region 20 to be heated, the electrodes E3, E4, of the second pair being, for example, in the center and the electrodes E1, E2 of the first pair and the electrodes E5, E6 of the third pair being respectively towards an initial end and a second end 21, 22 of the region 20 to be heated.

If, in the region 20 to be heated, we consider a point A located between the electrodes E2, E4 of the second pair and more towards the initial end 21 of the region 20 to be heated, the power dissipated in a small volume surrounding the point A is derived, to the major extent, from the energy supplied by the second generator G2, and to a smaller extent, from the energy supplied by the first generator G1. The contribution of the third generator G3 is even smaller owing to the fact that the corresponding fifth and sixth electrodes E5, E6 are further away from the point A. The power dissipated in the region A is in fact equal to the sum of the power values provided in this region A by each of the generators G1, G2, G3 and, by modifying the power controls 7 respectively belonging to each of the generators G1, G2, G3, it is possible to make variations in the power dissipated in A without excessively modifying the power supplied at a second point B. Since the second point B is, for example, located towards the initial end 21 between the first and second electrodes E1, E2 of the first generator G1, its temperature is hardly affected by a modification of the power of the third generator G3.

This point constitutes a major improvement over the apparatus of the prior art, comprising either one generator alone or several generators operating at only one frequency. In the latter case, since there is an exchange of high-frequency energy among the electrodes that belong to different generators, depending on the relative phase of these generators, it is difficult to make a precise forecast of the consequences entailed by modifying the power of a single generator.

It is thus possible, with a hyperthermic apparatus according to the invention, to make a simple modification or adjustment, in the course of treatment, of the distribution of the power dissipated. Increasingly complex temperature profiles can be obtained by increasing the number of generators operating at different frequencies.

FIG. 2 depicts the same general configuration of the hyperthermic apparatus 1, according to the invention, as that depicted in FIG. 1, but one which additionally comprises filters f1, f2, ..., f6, placed in series between at least one of the outputs of the generators G1, G2, G3, and the electrodes E1, E2, ..., E6.

The filters f1, ..., f6 constitute bandpass filters tuned to the operating frequencies F1, F2, F3 or the generators G1, G2, G3 to which they are linked.

In the non exhaustive example described, each filter f1, f6 is linked firstly, by one initial end 26 to the electrodes E1 to E6 respectively, and secondly by an opposite end 28 to the corresponding outputs of the generators, G1, G2, G3:

The initial output 10 of the first generator G1 is connected by a link 27 to the first filter f1, the second output 11 being connected by a link 27 to the second filter f2;

The third output 12 of the second generator G2 is connected to the third filter f3 by a link 27, the fourth output 13 being connected to the fourth filter f4 by a link 27;

The fifth output 14 of the third generator G3 is connected by a link 27 to the fifth filter f5, the sixth output 15 being linked to the sixth filter f6.

This serial arrangement of the filters f1, ..., f6 constitutes an important characteristic of the invention, made possible by the fact that the generators G1, G2, G3 operate at different frequencies F1, F2, F3, thus enabling each of these generators to display high impedance with respect to the other two generators. The result of this is that the power supplied by each of the generators is dissipated only in the load 6, formed by the biological tissues, i.e. in the region to be heated 20, and is not partially dissipated in the other generators as is the case in apparatuses of the prior art. This characteristic further provides for even greater mastery over the distribution of the dissipated power by making the generators G1, G2, G3 more independent of one another.

In the non-exhaustive example of the invention, the filters f1 to f6 are each composed of an inductive resistor L1 to L6 and a capacitor C1 to C6, placed in series, the values of which are selected in such a way that:

The first and second filters f1, f2 each resonate at the first frequency F1 of the first generator G2

The third and fourth filters f3, f4 resonate at the second frequency F2 of the second generator G2

The fifth and sixth filters f5, f6 resonate at the third frequency F3 of the third generator G3.

It must be noted that, in the non-exhaustive described, the first, second and third frequencies, F1, F2, F3 are respectively such that the second frequency F2, which is an intermediate frequency between the other two frequencies F1, F3, substantially represents the geometrical mean of the values of these other two frequencies F1, F3, that is, $F1 \cdot F3 = F2^2$; this fact being favourable to a simple embodiment of the filters f1, ..., f6.

It is observed in practice that a satisfactory decoupling of the generators G1, G2, G3 is obtained when each of the filters f1 to f6 displays, in series with the resistance offered by the biological tissue and for the frequencies F1, F2, F3 of the generators G1, G2, G3, other than its resonance frequency, an impedance which is substantially equal to or greater than ten time the resistance of the biological tissue.

FIG. 3 depicts an embodiment of the hyperthermic apparatus according to the invention, wherein each of the generators G1, G2, G3 comprises two half-generators or output amplifiers, respectively 31, 31' and 32, 32' and 33, 33', respectively receiving the signals of one and the same oscillator 34, 35, 66, with each of these oscillators 34, 35, 66 operating at the frequency F1, F2, F3 of the generators G1, G2, G3 to which it belongs. Each output amplifier 31, 31' ..., 33, 33' comprises a separate power-adjusting means 7', with which to adjust the power level of the wave produced by each of these output amplifiers, the output amplifiers of one and the same generator supplying signals in phase opposition with respect to a common ground, according to the diagram described further below:

The first amplifier 31 and the second amplifier 31' belonging to the first generator G1, each comprise a ground output 36 connected to the ground, an output 10 of the first amplifier 31 constituting the previously mentioned first output 10, being connected to the first electrode E1, an output 11 of the second amplifier 31' constituting the previously mentioned second output 11, being connected to the second electrode E2;

The third amplifier 32 and the fourth amplifier 32', belonging to the third generator G1, each comprise an ground output 36 connected to the ground, an output 12 of the third amplifier 32 constituting the previously mentioned third output 12 being connected to the third electrode E3, an output 13 of the fourth amplifier 32' constituting the previously mentioned fourth output 13 being connected to the fourth electrode E4;

The fifth amplifier 33 and the sixth amplifier 33', belonging to the third generator G3, each comprise an ground output 36 connected to the ground, an output 14 of the fifth amplifier 33 constituting the previously mentioned fifth output 14 being connected to the fifth electrode E5, an output 15 of the sixth amplifier 33' constituting the previously mentioned sixth output 15 being connected to the fourth electrode E6.

In the non-exhaustive example described, the outputs 10 to 15 of the generators G1, G2, G3 are connected to the electrodes E1 to E6 by means of the filters f1 to f6 and the links 27 are replaced by coaxial cables or coaxial lines, 45, 46, 47, 48, 49, 50, respectively. The external conductors 51 of these coaxial cables are connected to the ground common to the generators G1, G2, G3 and are also joined to one another at a common point 52 on the side of the electrodes E1 to E6. The impedance displayed by the biological tissues to each electrode E1 to E6 in relation to the common point 52 depends partly on the dimensions of these electrodes and the nature of the biologcal tissues. Typically, however, in deep hyperthermia, this impedance is essentially resistive and is equal to about 10 Ohms. Assuming that the generators G1, G2, G3 comprise, as they would do in a conventional way, output impedances of 50 Ohms, advantageous use can be made of coaxial cables 45 to 50 with a characteristic impedance of 25 Ohms, the lengths of these cables 11, 12, 13 corresponding to a quarter of the wave length ($\lambda/4$) of the first, second or third frequency F1, F2, F3 of the high-frequency wave transmitted. The impedance of 25 Ohms can be obtained, for example, by using two parallel-mounted coaxial cables each of which has a characteristic impedance of 50 Ohms.

A major additional advantage of this configuration lies in the fact that it makes it possible to reduce parasite radiation to very low values and that, since the elements are all at low impedance, it is possible improve the adaptations in a simple way.

Another major advantage lies in the fact that, since the generators G1, G2 and G3 are each separated into two parts formed by the amplifiers 31, 31', ..., 33, 33', their power can also be divided into two parts which also produce a power of 250 Watts, for example. Thus, each of these amplifiers can be made up of low-impedance, active semi-conductors which are thus more easily suited to loads made up of biological tissues than is the case with generators comprising electronic tubes such as the ones used when high power values are involved.

To give FIG. 3 greater clarity, the connection between the fourth filter f4 of the fourth electrode E4 and an end 53 of the fourth coaxial cable 48 belonging to the second generator G2 has not been depicted.

FIG. 4 depicts an alternative mode of embodiment of the invention illustrating the possibilities for connecting the generators G1, G2, G3 to the electrodes in a configuration which uses a minimum number of electrodes E1, E2, E3, while at the same time, making it possible, as in the preceding examples, to modify the distribution of the power dissipated.

In the non-exhaustive example described, the generators G1, G2, G3 are depicted according to the embodiment with two amplifiers, but it is also possible for each of them or one of them to comprise a single generator as depicted in FIGS. 1 and 2. For the clarity of figure 4, the generators G1, G2, G3 are connected to electrodes by means of simple links 27 but they can be equally well connected by the previously mentioned coaxial cables 45 to 50.

In this alternative mode of embodiment of the invention, the region 29 to be heated is surrounded by three electrodes E1, E2, E3 having a section which is substantially shaped like the arc of a circle, each of these electrodes being common to two generators G1, G2 or G1, G3 or G2, G3 according to the non-exhaustive example of this diagram described below:

The first electrode E1 is connected firstly, to the first output 10 of the first generator G1 by means of the first filter f1 and secondly, to the sixth output 15 of the third generator G3 by means of the sixth filter f6;

The second electrode E2 is connected firstly, to the second output 11 of the first generator G1 by means of the second filter f2, and secondly, to the third output 12 of the second generator G2 by means of the third filter f3.

The third electrode E3 is connected firstly, to the fourth output 13 of the second generator G2 by means of the fourth filter f4, and, secondly, to the fifth output 14 of the third generator G3 by means of the fifth filter f5.

The electrodes E1, E2, E3 extend along the region to be heated 20, along a length (not depicted) perpendicular to the plane of the figure, and energy is exchanged among the electrodes E1, E2, E3 along this length, essentially along the planes which are perpendicular to this length, i.e. parallel to the plane of the figure.

This configuration can be used to set the distribution of power with a minimum number of electrodes and, consequently, to adjust the temperature in the region 20 to be heated, the contribution of each of the generators G1, G2, G3 at each electrode E1, E2, E3 being independently adjustable, without producing any reaction in the other generators and without producing any other effects in the region to be heated 20 than those which are directly linked to the modification of the power exerted on one of the generators.

The example of FIG. 4 shows that it is possible to connect an electrode, the third electrode E3 for example, to two outputs 13, 14, or more outputs of different generators G2, G3.

What is claimed is:

1. Apparatus for hyperthermic treatment comprising high-frequency generating means connected to electrodes capable of being attached to a patient wherein the said generating means comprise at least two generators operating at different frequencies, the values of which are sufficiently distant from each to prevent the generators from mutually driving or interfering with one another's frequencies, the operating frequencies of the generators having values such that they do not constitute a harmonic frequency of one and the same fundamental frequency, and wherein the said generators comprise two outputs each linked to one electrode, at least one of the said outputs of at least one generator being connected to the said electrode by means of a bandpass filter, the resonance frequency of the said filter corresponding substantially to the operating frequency of the generator to which it is connected.

2. Hyperthermic apparatus according to the claim 1, wherein the said generators each comprise a power-adjusting means.

3. Hyperthermic apparatus according to the claim 1, wherein at least one of the said generators comprise two output amplifiers operating at the same frequency.

4. Hyperthermic apparatus according to the claim 3, wherein the said output amplifiers each comprise a power-adjusting means.

5. Hyperthermic apparatus according to the claim 4, wherein each output amplifier comprises an output linked to an electrode and an output linked to ground.

6. Hyperthermic apparatus according to the claim 1, wherein the said generators are linked to the said electrodes by means of coaxial lines, the length of which is substantially a quarter of the length of the waves corresponding to the frequency of the generator to which they are connected.

7. Hyperthermic apparatus according to the claim 6, wherein the said coaxial lines have a characteristic impedance which is substantially equal to 25 Ohms.

8. Hyperthermic apparatus according to claim 1, wherein the said generators have at least one output linked to the same electrode

* * * * *